US008840925B2

(12) United States Patent
Venkatesh et al.

(10) Patent No.: US 8,840,925 B2
(45) Date of Patent: Sep. 23, 2014

(54) ORALLY DISINTEGRATING TABLET COMPOSITIONS OF LAMOTRIGINE

(75) Inventors: Gopi M. Venkatesh, Vandalia, OH (US); Nehal H. Vyas, Huber Heights, OH (US); Michael Gosselin, Loveland, OH (US); Jin-Wang Lai, Springboro, OH (US)

(73) Assignee: Aptalis Pharmatech, Inc., Vandalia, OH (US)

( * ) Notice: Subject to any disclaimer, the term of this patent is extended or adjusted under 35 U.S.C. 154(b) by 0 days.

(21) Appl. No.: 13/455,942

(22) Filed: Apr. 25, 2012

(65) Prior Publication Data

US 2013/0108703 A1   May 2, 2013

Related U.S. Application Data

(63) Continuation of application No. 12/628,677, filed on Dec. 1, 2009, now Pat. No. 8,647,656, which is a continuation of application No. 12/166,757, filed on Jul. 2, 2008, now Pat. No. 7,919,115.

(60) Provisional application No. 60/929,536, filed on Jul. 2, 2007.

(51) Int. Cl.
   *A61K 9/16* (2006.01)
   *A61K 9/26* (2006.01)
   *A61K 9/46* (2006.01)
   *A61K 9/00* (2006.01)
   *A61K 9/50* (2006.01)
   *A61K 9/20* (2006.01)

(52) U.S. Cl.
   CPC ............. *A61K 9/5005* (2013.01); *A61K 9/2077* (2013.01); *A61K 9/0056* (2013.01); *A61K 9/5042* (2013.01); *A61K 9/2081* (2013.01); *A61K 9/5047* (2013.01); *A61K 9/5026* (2013.01); *A61K 9/5084* (2013.01); *A61K 9/5031* (2013.01)
   USPC ............................ 424/466; 424/469; 424/490

(58) Field of Classification Search
   None
   See application file for complete search history.

(56) References Cited

U.S. PATENT DOCUMENTS

| 5,556,639 | A | 9/1996 | Fielden |
| 6,194,000 | B1 | 2/2001 | Smith et al. |
| 7,919,155 | B2 * | 4/2011 | Iftime et al. ............... 428/29 |
| 2004/0043996 | A1 | 3/2004 | Nadkarni |
| 2005/0118286 | A1 | 6/2005 | Suffin et al. |
| 2005/0232988 | A1 * | 10/2005 | Venkatesh et al. ............ 424/464 |
| 2006/0105038 | A1 | 5/2006 | Lai et al. |
| 2006/0105039 | A1 | 5/2006 | Lai et al. |
| 2006/0165781 | A1 * | 7/2006 | Ferran ............................ 424/464 |
| 2006/0182796 | A1 | 8/2006 | Wu et al. |
| 2007/0148211 | A1 | 6/2007 | Altreuter et al. |
| 2009/0092672 | A1 | 4/2009 | Venkatesh et al. |
| 2010/0303905 | A1 | 12/2010 | Venkatesh et al. |

FOREIGN PATENT DOCUMENTS

| WO | WO 03/104192 A2 | 12/2003 |
| WO | WO 2004/103340 A1 | 12/2004 |
| WO | WO 2005109990 A2 * | 11/2005 |
| WO | WO 2006/047493 A2 | 5/2006 |
| WO | WO 2006047493 A2 * | 5/2006 |
| WO | WO 2006/092812 A2 | 9/2006 |

OTHER PUBLICATIONS

Applied Biopharmaceutics & Pharmacokinetics, 5th Ed., L. Shargel, S Wu-Pong, and A. Yu, McGraw-Hill, New York, 2005, pp. 161-167, 461-463.
Communication from the Intellectual Property Office of New Zealand for corresponding New Zealand Patent Application No. 582458, mailed on Nov. 3, 2010.
Explanation of relevant portion of Opposition in corresponding Chile Patent Application No. 1966-2008.
Explanation of Technical Report in corresponding Panama Patent Application No. 87869 (Jul. 2, 2008).
International Search Report, PCT Appl. No. PCT/US08/6900, 2 pages (Sep. 23, 2008).
Notice of Paragraph IV Certification, 22 pages, Par Pharmaceutical, Inc. (Aug. 28, 2012).
Office Action in corresponding Thailand Patent Application No. 0801003378 (Mar. 24, 2010), Translation.
Opposition in corresponding Chile Patent Application No. 1966-2008, Translation.
Partial English translation of relevant portion of Office Action in corresponding Thailand Patent Application No. 0801003378 (Mar. 24, 2010).
Supplementary European Search Report, EP Appl. No. 08772352.4, 6 pages (Oct. 10, 2012).
Technical Report in corresponding Panama Patent Application No. 87869 (Jul. 2, 2008), Translation.
Written Opinion of the International Searching Authority, PCT Appl. No. PCT/US08/69000, 7 pages (Sep. 23, 2008).

* cited by examiner

*Primary Examiner* — Susan Tran
(74) *Attorney, Agent, or Firm* — Cooley LLP

(57) ABSTRACT

The compositions of the present invention composition comprise a therapeutically effective amount of particles comprising lamotrigine, in combination with granules comprising a disintegrant, and a sugar alcohol and/or a saccharide. These compositions are useful in treating epilepsy and bipolar disorder, particularly for patients with dysphagia, and to improve compliance with bipolar patients.

22 Claims, 6 Drawing Sheets

ORALLY DISINTEGRATING TABLET COMPOSITIONS OF LAMOTRIGINE

CROSS REFERENCE TO RELATED APPLICATIONS

This application claims the benefit of U.S. Provisional Patent Application No. 60/929,536 filed Jul. 2, 2007, and is a continuation of U.S. application Ser. No. 12/628,677, filed Dec. 1, 2009, which is a continuation of U.S. application Ser. No. 12/166,757 filed Jul. 2, 2008, now U.S. Pat. No. 7,919,115, the entire disclosures of which are herein incorporated by reference in their entirety for all purposes.

TECHNICAL FIELD

This invention relates to a pleasant tasting, orally dissolving or disintegrating tablet (ODT) composition comprising lamotrigine, useful for the treatment of epilepsy and mood disorders such as bipolar disorder.

BACKGROUND OF THE INVENTION

Dysphagia, or difficulty in swallowing due to fear of choking, is common among all age groups. For example, it is observed in about 35% of the general population, as well as an additional 30-40% of elderly institutionalized patients and 18-22% of all persons in long-term care facilities, many of whom are required to consume medications on a regular basis to maintain their quality of life. This leads to poor or even non-compliance with oral treatments and thus has a negative impact on the efficacy of oral treatments.

The primary treatment objectives for patients with epilepsy are maintenance of adequate anti-epileptic drug levels and prevention of subsequent seizures. In patients with mood disorders such as bipolar disorder, the objective is to prevent relapse and stabilize mood. In both cases, compliance with the prescribed dosage regimen is essential for the maintenance of therapeutic blood levels.

Lamotrigine is an anticonvulsant drug used in the treatment of epilepsy and bipolar disorder, and is used to treat partial seizures, primary and secondary tonic-clonic seizures, and seizures associated with Lennox-Gastaut syndrome. Lamotrigine is chemically 3,5-diamino-6-(2,3,-dichlorophenyl)-1,2,4-triazine). It has an empirical formula of $C_9H_7N_5Cl_2$, a molecular weight of 256.09 and the structural formula shown below:

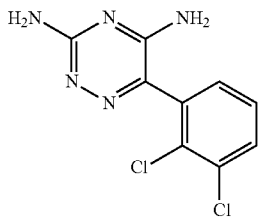 [SMILES: Nc1nnc(-c2cccc(Cl)c2Cl)c(N)n1]

The preparation of lamotrigine is described in U.S. Pat. No. 4,602,017, which is incorporated in its entirety herein by reference for all purposes. Lamotrigine is very slightly soluble in water (~0.17 mg/ml at 25° C.; ~0.57 mg/ml at 37° C.), but is significantly more soluble in 0.01N HCl (~3 mg/ml at 25° C.) and 0.1N HCl (~4 mg/ml at 25° C.).

SUMMARY OF THE INVENTION

In one embodiment, the present invention is directed to an orally disintegrating tablet (ODT) composition comprising a therapeutically effective amount of lamotrigine, wherein after administration said composition substantially disintegrates in the oral cavity of a patient and provides a lamotrigine release profile which is substantially the same as the lamotrigine release profile of an immediate release lamotrigine composition.

In another embodiment, the present invention is directed to an orally disintegrating tablet (ODT) composition comprising a therapeutically effective amount of lamotrigine coated with a taste-masking layer, in combination with granules comprising a disintegrant, a sugar alcohol, and/or a saccharide, wherein after administration said composition substantially disintegrates in the oral cavity of a patient and provides a lamotrigine release profile which is substantially the same as the lamotrigine release profile of an immediate release lamotrigine composition.

In another embodiment, the present invention is directed to a method of preparing compositions comprising particles which comprise lamotrigine, and granules comprising a disintegrant, a sugar alcohol and/or a saccharide, wherein the method comprises (a) coating particles comprising lamotrigine with a taste-masking layer; (b) preparing granules comprising a disintegrant, a sugar alcohol, and/or a saccharide; (c) mixing the coated particles of step (a) with the granules of step (b) and optionally other pharmaceutically acceptable ingredients; and (d) compressing the blend of step (c) into tablets.

In yet another embodiment, the present invention is directed to a method of treating mood disorders, or treating or preventing seizures comprising administering to a patient in need thereof a therapeutically effective amount of a composition comprising a therapeutically effective amount of particles comprising lamotrigine, in combination with granules comprising a disintegrant, a sugar alcohol, and/or a saccharide.

These and other embodiments, advantages and features of the present invention become clear from the detailed description and examples provided in subsequent sections.

DETAILED DESCRIPTION OF THE INVENTION

Figure 1:
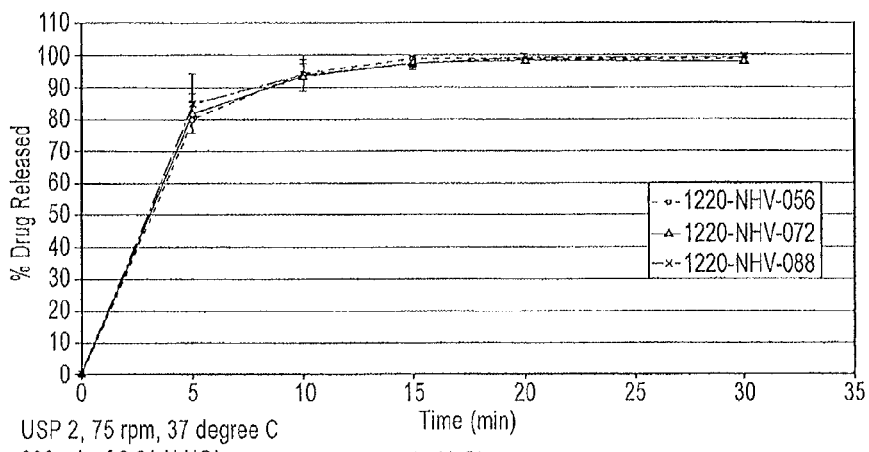
FIG. 1 shows dissolution profiles for orally disintegrating tablet (ODT) formulations comprising lamotrigine microgranules of Example 3.

The term "drug", "active" or "active pharmaceutical ingredient" as used herein includes a pharmaceutically acceptable and therapeutically effective compound (e.g., lamotrigine), pharmaceutically acceptable salts, stereoisomers and mixtures of stereoisomers, solvates (including hydrates), and/or esters thereof (e.g., of lamotrigine).

The terms "orally disintegrating tablet", "orally dispersing tablet", or "ODT" refer to a solid dosage form of the present invention, which disintegrates rapidly in the oral cavity of a patient after administration, without chewing. The rate of disintegration can vary, but is faster than the rate of disintegration of conventional solid dosage forms or chewable solid dosage forms (i.e., tablets or capsules) which are intended to be swallowed immediately after administration. ODT compositions of the present invention can contain pharmaceutically acceptable ingredients which swell, dissolve or otherwise facilitating the disintegration or dissolution of the ODT composition. Such ingredients can include pharmaceutical a disintegrant, a sugar alcohol, a saccharide, or a mixture thereof, a water-soluble binder, a meltable solid (e.g., a wax), which can release the lamotrigine upon entering the stomach, etc.

The term "about", as used herein to refer to a numerical quantity, includes "exactly". For example, "about 60 seconds" includes 60 seconds, exactly, as well as values close to 60 seconds (e.g., 50 seconds, 55 seconds, 59 seconds, 61 seconds, 65 seconds, 70 seconds, etc.). when the term "about" is used in reference to a range of values, the term "about" refers to both the minimum and maximum value of the range (e.g., "about 1-50 μm" means "about 1 μm to about 50 μm").

In most embodiments, the ODT compositions of the present invention comprise a therapeutically effective amount of lamotrigine coated with a taste-masking layer, e.g. in the form of a tablet further comprising disintegrant-containing granules. Upon administration of an ODT tablet of the present invention to the oral cavity of a patient, the tablet disintegrates rapidly in the patient's oral cavity into taste masked, lamotrigine containing particles while the sugar alcohol/saccharide containing granules rapidly dissolve to form a smooth suspension that can be readily swallowed.

The rate of disintegration of the ODT compositions of the present invention in the oral cavity of a patient can be on the order of about 60 seconds or less, about 50 seconds or less, about 40 seconds or less, about 30 seconds or less, about 20 seconds or less, or about 10 seconds or less.

Alternatively, the rate of disintegration of the ODT compositions of the present invention can be measured using various in vitro test methods, for example the USP <701> Disintegration Test. When using the USP <701> Disintegration Test, the rate of disintegration of ODT compositions is faster than that of conventional oral, non-ODT compositions, for example about 60 seconds or less, about 30 seconds or less, about 20 seconds or less, or about 10 seconds or less.

The rate of dissolution of the lamotrigine in the ODT compositions of the present invention can be evaluated using the United States Pharmacopoeia Apparatus 2 (paddles @ 75 rpm in 900 mL of 0.01N HCl buffer). When using the United States Pharmacopoeia Apparatus 2 test, the rate of dissolution of the drug (e.g., lamotrigine) is comparable to that of conventional, non-ODT compositions, for example about 70% or more, about 75% or more, about 80% or more, about 85% or more, about 90% or more, about 95% or more, or about 100% of the total amount of lamotrigine is released in 30 min.

The term "substantially disintegrates" means a level of disintegration amounting to disintegration of at least about 50%, at least about 60%, at least about 70%, at least about 80%, at least about 90%, or about 100% disintegration of the ODT composition.

Figure 2:
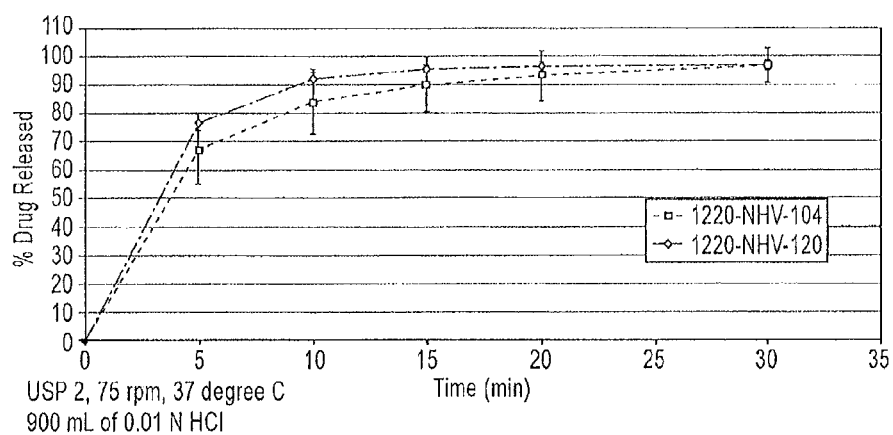
FIG. 2 shows dissolution profiles for orally disintegrating tablet (ODT) formulations comprising lamotrigine microcapsules of Example 3.
Figure 6:
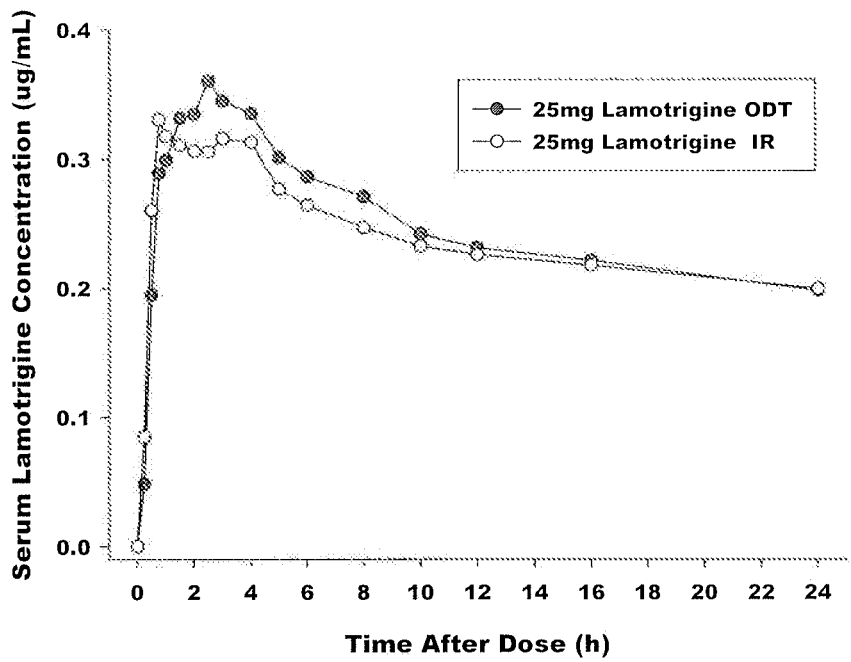
FIG. 6 compares the plasma concentration-time profiles for lamotrigine ODT comprising taste-masked microparticles vs. Lamictal® IR of Example 5.
Figure 6:
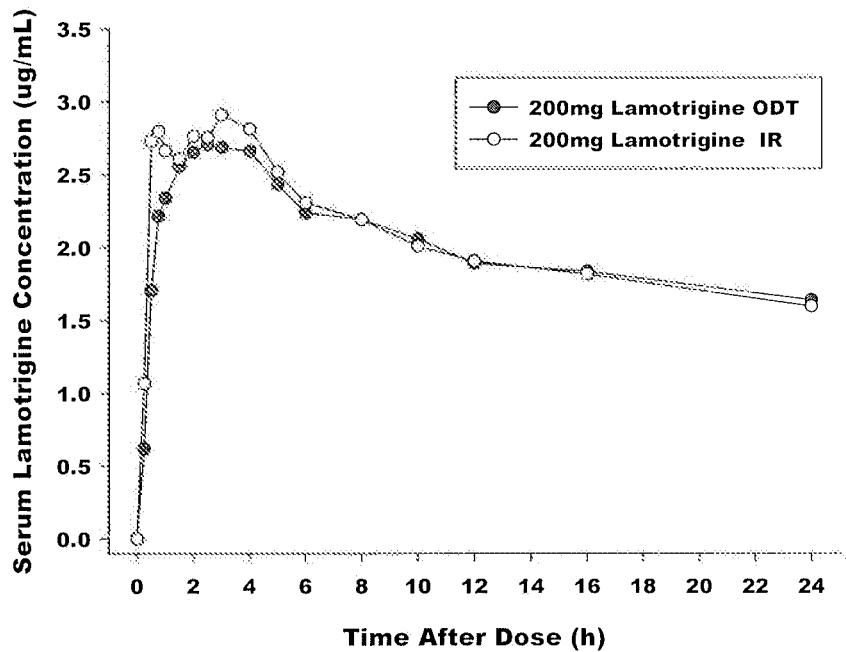
Figure 7:
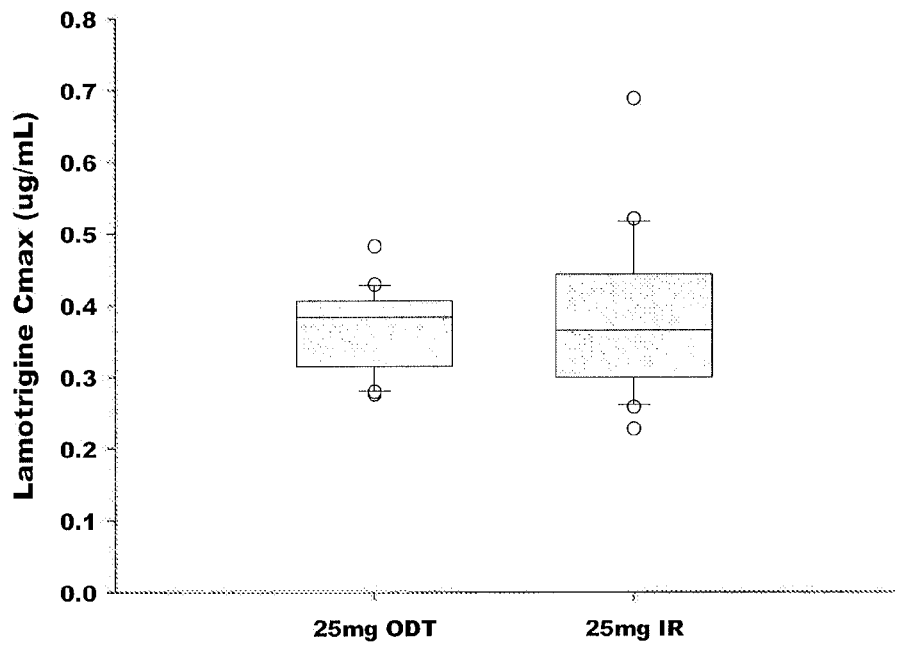
FIG. 7 compares the mean $C_{max}$ results for lamotrigine ODT comprising taste-masked microparticles vs. Lamictal® IR of Example 5.
Figure 7:
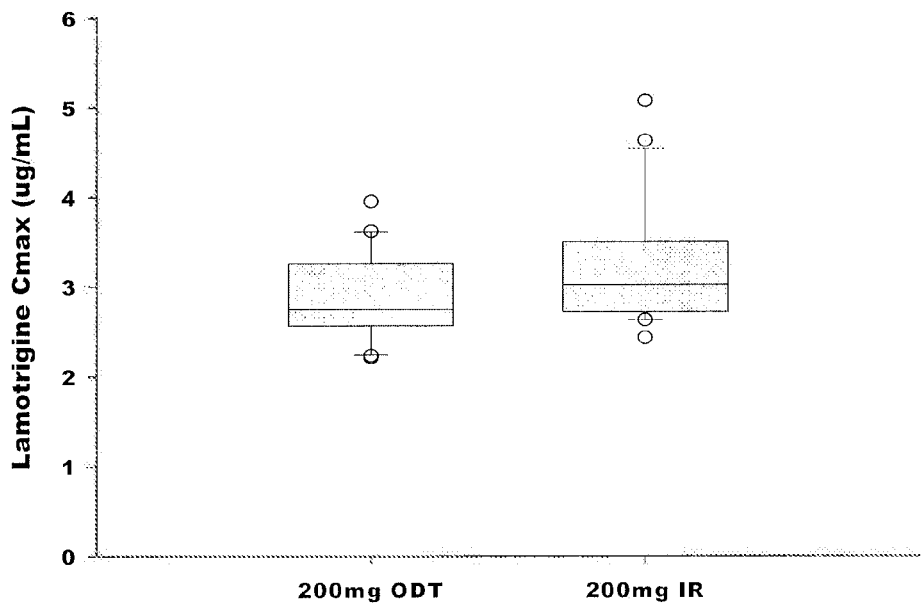
Figure 8:
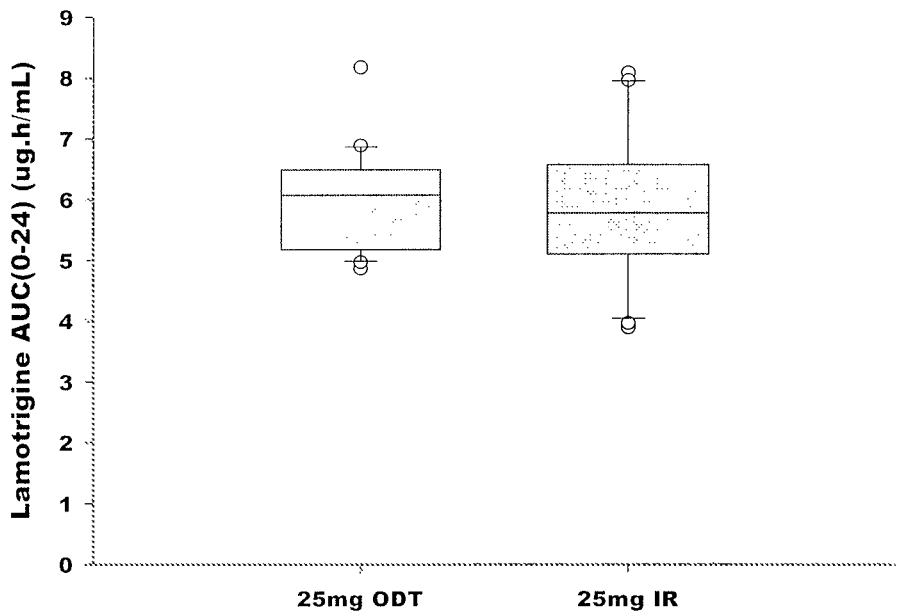
FIG. 8 compares the mean $AUC_{(0-24)}$ results for lamotrigine ODT comprising taste-masked microparticles vs. Lamictal® IR of Example 5.
Figure 8:
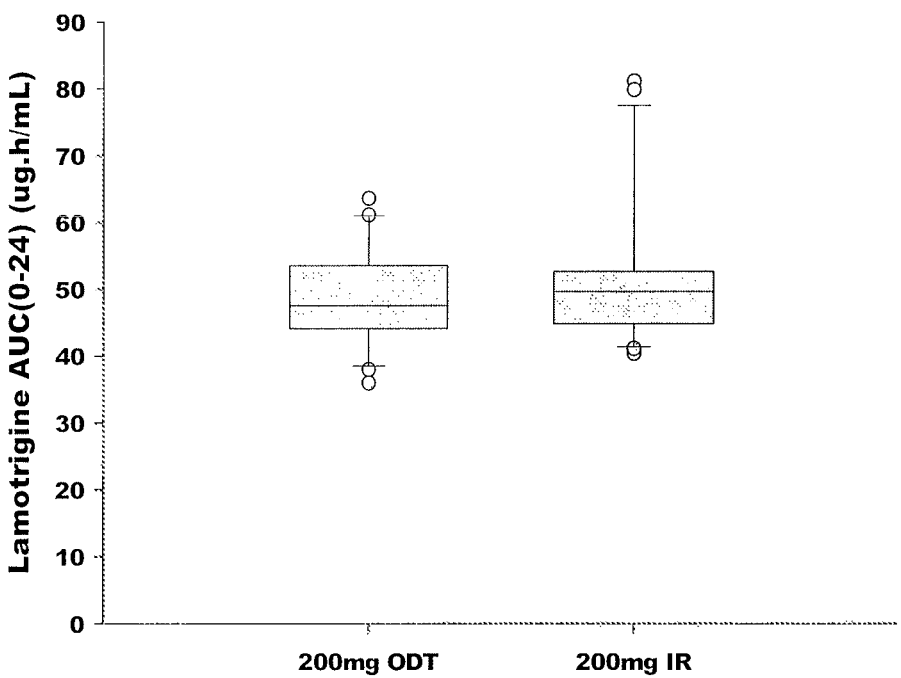

The term "lamotrigine release profile" refers to the dissolution profile of a lamotrigine-containing composition (e.g., as shown in FIGS. 1 and 2), and/or the plasma concentration-time profile (e.g., as shown in FIG. 6), and/or the $C_{max}$ or mean $AUC_{(0-24)}$ values (e.g., as shown in FIGS. 7 and 8). The ODT compositions of the present invention provide lamotrigine release profiles which are substantially the same as the lamotrigine release profiles of non-ODT immediate release oral lamotrigine compositions having the same dosage of lamotrigine (e.g., Lamictal®). Thus, an ODT composition of the present invention which has a dissolution profile, plasma concentration-time profile, $C_{max}$, or $AUC_{(0-24)}$, or any combination or subcombination of these parameters, which is substantially the same as a non-ODT immediate release lamotrigine composition, has a lamotrigine release profile which is substantially the same as a non-ODT immediate release lamotrigine composition.

By "substantially the same", we mean that the lamotrigine release profile of the ODT compositions of the present invention (as defined) varies by 25% or less from the lamotrigine release profile of non-ODT immediate release oral lamotrigine compositions having the same dosage of lamotrigine. Alternatively, the term "substantially the same" means a lamotrigine release profile which is statistically indistinguishable from the lamotrigine release profile of non-ODT immediate release oral lamotrigine compositions having the same dosage of lamotrigine.

The term "non-ODT immediate release lamotrigine composition" refers to non-ODT compositions containing lamotrigine, which do not contain extended release or controlled release coatings to delay release of the lamotrigine. For example, non-ODT immediate release compositions include conventional tablets intended to be swallowed and absorbed in the gastrointestinal tract, chewable tablets which require mastication in order to break apart the tablet structure, and the various types of capsules known in the art.

A microparticle as used in the present invention refers to a particle or a granule with an average particle size of not more than 400 μm, more particularly not more than 300 μm. The terms, particle, microparticle, granule and/or microgranule, are herein used interchangeably to mean a particle with a mean particle size of not more than 400 μm, irrespective of whether said particle contains lamotrigine and/or a sugar alcohol or not. The term "Lamotrigine Microcaps" refers specifically to taste-masked lamotrigine-containing particles with a mean particle size of not more than 400 μm.

The microparticles can be described as primary particles or secondary particles. Primary particles are unagglomerated, whereas secondary particles are agglomerated primary particles. Thus, primary particles are generally smaller than secondary particles. Primary particles of lamotrigine can have an average particle size ranging from about 1-300 μm, including about 1-50 μm, about 1-100 μm, and about 1-150 μm.

Unless indicated otherwise, all percentages and ratios are calculated by weight. Unless indicated otherwise, all percentages and ratios are calculated based on the total composition.

As discussed above, the primary treatment objectives for patients with epilepsy are maintenance of adequate anti-epileptic drug levels and prevention of subsequent seizures. In patients with bipolar disorder, the objective is to prevent relapse and stabilize mood. In both cases, compliance with the prescribed dosage regimen is essential for the maintenance of therapeutic blood levels. One approach to improving compliance is to administer the lamotrigine in the form of an orally disintegrating tablet (ODT) which readily disintegrates in the mouth forming a smooth, palatable suspension containing lamotrigine so that it can be easily swallowed (i.e., for patients with dysphagia). Similarly, the ODT form will also prevent "checking" if it disintegrates too rapidly to be discarded. Thus, an ODT formulation with an in vitro disintegration time of ≤30 seconds (e.g., using the USP <701> Disintegration Test), would be ideal in order to improve patient acceptability/compliance, and to prevent the medication from being discarded after "checking", particularly in the elderly and institutionalized patients with bipolar disorder.

However, even if an ODT formulation has an acceptable disintegration time, it must also be palatable, e.g. have acceptable taste and mouthfeel characteristics. For bitter tasting drugs such as lamotrigine, the ODT formulation may include a taste-masking polymer to improve the taste characteristics of the formulation, as well as a disintegrant, sugar alcohol, a saccharide, or a mixture thereof, to provide rapid disintegration in the oral cavity as well as a "creamy" mouthfeel. In addition, the ODT formulation must also provide acceptable pharmacokinetics and bioavailability to provide the desired therapeutic effect. These desired properties of an ODT formulation can be contradictory, in that components of the formulation that provide acceptable taste-masking properties can inhibit or delay release of the lamotrigine, thereby providing unacceptable pharmacokinetic properties. Conversely, components of the formulation that promote release of the lamotrigine result in undesirable taste or mouthfeel properties. Accordingly, an acceptable ODT formulation must balance these contradictory characteristics in order to provide a palatable (e.g., taste-masked), fast disintegrating composition with acceptable pharmacokinetics.

The ODT compositions of the present invention are palatable lamotrigine formulations with good disintegration characteristics and pharmacokinetics, which provide improved compliance for patients in need thereof who have difficulty swallowing conventional lamotrigine tablets or for patients with bipolar disorder, compared to non-ODT lamotrigine-containing compositions.

The compositions of the present invention can comprise any combination of a therapeutically effective amount of lamotrigine and one or more pharmaceutically acceptable ingredients which provide an ODT composition as defined herein. For example, lamotrigine can be combined with a disintegrant, a sugar alcohol, and/or a saccharide, and/or binder, whereby the sugar alcohol, disintegrant, and hinder swell and/or dissolve in the saliva of a patient's oral cavity, thereby forming a smooth easy-to-swallow suspension containing the lamotrigine. Additionally, a synthetic sweetener such as sucralose, a favoring agent such as a cherry flavor, and/or the same or a different disintegrant are included to promote rapid disintegration and to further improve organoleptic properties of the lamotrigine ODT formulation.

In one embodiment, the ODT compositions of the present invention comprise granules (e.g., microgranules or microparticles) prepared by the steps comprising (a) granulating lamotrigine and/or encapsulating lamotrigine-containing cores, (b) blending the granules or encapsulated lamotrigine-containing cores with granules comprising a disintegrant, a sugar alcohol and/or a saccharide (hereafter referred to as rapidly dispersing microgranules), and (c) compressing the mixture into an ODT.

In another embodiment, the lamotrigine-containing granules of the present invention can be granules comprising lamotrigine crystals and a film-forming binder, e.g., prepared by granulation. The lamotrigine crystals can have an average particle size ranging from about 1-300 µm, for example about 1-50 µm, about 1-100 µm, about 1-150 µm, about 1-200 µm, about 1-250 µm, about 50-100 µm, about 50-150 µm, about 50-200 µm, about 50-250 µm, about 50-300 µm, about 100-150 µm, about 100-200 µm, about 150-200 µm, about 150-250 µm, about 150-300 µm, about 200-250 µm, about 200-300 µm, or about 250-300 µm.

The film-forming binder can comprise any suitable binder used in granulation. Non-limiting examples of suitable film-forming binders include water-soluble, alcohol-soluble or acetone/water soluble binders, e.g. polyvinylpyrrolidone (PVP), corn starch, polyethylene oxide, polyethylene glycol, hydroxypropyl methylcellulose (HPMC), methylcellulose, or hydroxypropylcellulose (HPC). The amount of film-forming binder in the lamotrigine-containing granules can range from about 0.5% to about 10%, including about 0.5%-1%, about 0.5%-2%, about 0.5%-5%, about 0.5%-7%, about 1%-2%, about 1%-5%, about 1%-7%, about 1%-10%, about 2%-5%, about 2%-7%, about 2%-10%, about 5%-7%, about 5%-10%, and about 7%-10%.

The lamotrigine-containing granules of the present invention can also include other pharmaceutically acceptable ingredients, for example, fillers or diluents. Non-limiting examples of other pharmaceutically acceptable ingredients for the lamotrigine-containing granules include, for example, mannitol, lactose, microcrystalline cellulose, potassium sulfate, calcium phosphate, modified starch, and mixtures thereof. The amount of other pharmaceutically acceptable ingredients (e.g. fillers or diluents) in the lamotrigine-containing granules can range from about 5%-80%, including about 5%-70%, about 5%-60%, about 5%-50%, about 5%-40%, about 5%-30%, about 5%-20%, about 5%-15%, about 5%-10%, about 10%-70%, about 10%-60%, about 10%-50%, about 10%-40%, about 10%-30%, about 10%-20%, about 10%-15%, about 20%-70%, about 20%-60%, about 20%-50%, about 20%-40%, about 20%-30%, about 20%-25%, about 30%-70%, about 30%-60%, about 30%-50%, about 30%-40%, about 30%-35%, about 40%-70%, about 40%-60%, about 40%-50%, about 40%-45%, about 50%-70%, about 50%-60%, about 50%-55%, about 60%-70%, or about 60%-65%.

The lamotrigine-containing granules of the present invention can be prepared by any suitable method. For example, the lamotrigine-containing granules can be prepared by granulation of lamotrigine crystals, one or more disintegrants, and one or more fillers (e.g., sugar alcohol, saccharide and/or microcrystalline cellulose) in a high shear granulator or a fluid-bed granulator using a solution of one or more polymeric binders, and dried in fluid bed equipment or on trays in a conventional oven to produce the lamotrigine-containing granules.

The ODT compositions of the present invention include rapidly dispersing granules comprising a disintegrant and a sugar alcohol and/or a saccharide. Non limiting examples of suitable disintegrants for the disintegrant-containing granules can include disintegrants or so-called super-disintegrants, e.g. crospovidone (crosslinked PVP), sodium starch glycolate, crosslinked sodium carboxymethyl cellulose, low substituted hydroxypropylcellulose, and mixtures thereof. The amount of disintegrant in the rapidly dispersing granules can range from about 1%-10%, or about 5%-10% of the total weight of the rapidly dispersing granules, including all ranges and subranges therebetween.

Sugar alcohols are hydrogenated forms of carbohydrates in which the carbonyl group (i.e., aldehyde or ketone) has been reduced to a primary or secondary hydroxyl group. Non-limiting examples of suitable sugar alcohols for the rapidly dispersing granules of the ODT compositions of the present invention can include e.g. arabitol, isomalt, erythritol, glycerol, lactitol, mannitol, sorbitol, xylitol, maltitol, and mixtures thereof. The term "saccharide" is synonymous with the term "sugars" includes monosaccharides such as glucose, fructose, the lactose, and ribose; and disaccharides such as sucrose, lactose, maltose, trehalose, and cellobiose. In one embodiment, non-limiting examples of suitable saccharides for use on the compositions of the present invention can include e.g. lactose, sucrose, maltose, and mixtures thereof. In another embodiment, the rapidly dispersing granules comprise at least one disintegrant in combination with a sugar alcohol. In another embodiment, the rapidly dispersing granules comprise at least one disintegrant in combination with a saccharide. In yet another embodiment, the disintegrant-containing granules comprise at least one disintegrant in combination with a sugar alcohol and a saccharide. The amount of sugar alcohol and/or saccharide in the rapidly dispersing granules ranges from about 99%-90%, or about 95%-90% of the total weight of the disintegrant-containing granules, including all ranges and subranges therebetween. In one embodiment, the average particle size of a sugar alcohol and/or saccharide is 30 µm or less, for example about 1-30 µm, about 5-30 µm, about 5-25 µm, about 5-20 µm, about 5-15 µm, about 5-10 µm, about 10-30 µm, about 10-25 µm, about 10-20 µm, about 10-15 µm, about 15-30 µm, about 15-25 µm, about 15-20 µm, about 20-30 µm, about 20-25 µm, or about 25-30 µm.

The rapidly dispersing granules of the present invention can be prepared by any suitable method. For example, the rapidly dispersing granules can be prepared by granulation of one or more disintegrants and one or more sugar alcohols and/or saccharides in a high shear granulator, and dried in fluid bed equipment or on trays in a conventional oven to produce the rapidly dispersing granules, e.g. in the form of rapidly-dispersing microgranules. Rapidly-dispersing microgranules can also be produced by the method described in U.S. patent application Ser. No. 10/827,106 filed Apr. 19, 2004, which is herein incorporated by reference in its entirety for all purposes.

The compositions of the present invention contain an amount of rapidly dispersing granules and/or the mixture of a disintegrant and a sugar alcohol and/or a saccharide sufficient to provide a suitable rate of disintegration in the oral cavity of a patient forming a smooth, palatable, easy-to-swallow suspension containing lamotrigine particles. The amount of a disintegrant in the rapidly dispersing granules and/or the amount of disintegrant-sugar alcohol/saccharide combination in relation to lamotrigine in the compositions of the present invention can be adjusted to provide a suitable disintegration rate, as well as to form a smooth, palatable, easy-to-swallow suspension containing lamotrigine particles. For example, the compositions of the present invention contain an amount of disintegrant-sugar alcohol/saccharide combination in relation to lamotrigine sufficient to provide an in vitro disintegration time of about ≤30 seconds (USP <701> Disintegration Test).

The amount of rapidly dispersing granules or the amount of disintegrant-sugar alcohol/saccharide combination in relation to the lamotrigine can vary depending upon the desired disintegration rate and the desired organoleptic properties including taste-masking, mouthfeel and aftertaste. The amount of disintegrant-sugar alcohol/saccharide combination in the compositions of the present invention can range from about 40% to about 95%, including about 40%, about 45%, about 50%, about 55%, about 60%, about 65%, about 70%, about 75%, about 80%, about 85%, about 90%, and about 95%, inclusive of all values, ranges, and subranges therebetween. In one embodiment, the amount of disintegrant-sugar alcohol/saccharide combination is about 60-70% of the total weight of the composition. In another embodiment, the amount of disintegrant-sugar alcohol/saccharide combination is about 65% by weight.

Likewise, the compositions of the present invention should contain a sufficient quantity of lamotrigine-containing granules or taste-masked lamotrigine-containing cores to provide a therapeutically effective dose of lamotrigine. The amount of lamotrigine in the lamotrigine-containing granules or taste-masked lamotrigine-containing cores and/or the amount of lamotrigine-containing granules or the taste-masked cores in the ODT compositions of the present invention can be adjusted to provide a therapeutically effective dose of lamotrigine.

The amount of lamotrigine in the ODT compositions of the present invention can range from about 5% to about 50%, including about 5%, about 10%, about 15%, about 20%, about 25%, about 30%, about 35%, about 40%, about 45%, and about 50%, inclusive of all values, ranges, and subranges therebetween. In one embodiment, the amount of lamotrigine-containing granules in the ODT compositions of the present invention is about 30% by weight of the ODT composition.

In another embodiment, the lamotrigine-containing granules of the present invention can be in the form of lamotrigine-layered beads. Lamotrigine-layered beads comprise a core, e.g. a pharmaceutically acceptable sugar bead, coated with a lamotrigine layer. Such lamotrigine-layered beads can be prepared, for example, by dissolving or suspending lamotrigine in a polymeric binder solution, which is then sprayed or coated onto inert particles (e.g., sugar spheres or cellulose spheres (Celphere®)). Suitable polymeric binders include any of those disclosed herein, for example starches, modified celluloses (e.g., hydroxypropylcellulose, carboxymethylcellulose sodium), alginic acid, polyvinyl pyrrolidone (povidone), and mixtures thereof. The amount of lamotrigine in the lamotrigine layer, and the thickness of the lamotrigine layer can be modified to provide a therapeutically effective dose of lamotrigine. The lamotrigine-containing layer comprises about 90%-99% lamotrigine, and about 1% to about 10% binder.

In another embodiment, the compositions of the present invention can comprise lamotrigine particles (e.g., crystals), coated with a taste-masking layer. The taste-masking layer (as described herein) can be applied to the lamotrigine particles by any suitable method, for example coacervation or fluidized bed coating methods.

The compositions of the present invention may comprise a mixture of the lamotrigine-containing granules or taste-masked lamotrigine-containing particles (e.g., taste-masked lamotrigine-containing granules, lamotrigine crystals, or lamotrigine-layered beads as described herein) and the rapidly-dispersing granules. The compositions of the present invention may further comprise one or more pharmaceutically acceptable, flavoring agents. Non-limiting examples of such flavoring agents include e.g. cherry, spearmint, orange, or other acceptable fruit flavors, or mixtures of cherry, spearmint, orange, and other acceptable fruit flavors, at up to about 3% based on the tablet weight. In addition, the compositions of the present invention is can also include one or more sweeteners such as aspartame, sucralose, or other pharmaceutically acceptable sweeteners, or mixtures of such sweeteners, at up to about 2% by weight, based on the tablet weight. Furthermore, the compositions of the present invention can include one or more FD&C colorants at up to 0.5% by weight, based on the tablet weight.

In addition, the compositions of the present invention can also include an additional disintegrant, in addition to the disintegrant in the disintegrant-containing granules (e.g., lamotrigine containing and/or rapidly-dispersing granules). The additional disintegrant can be the same disintegrant used in the disintegrant-containing granules, or a different disintegrant. The additional disintegrant may be present in the compositions of the present invention at up to about 10% based on the tablet weight.

The compositions of the present invention can also include a pharmaceutically acceptable microcrystalline cellulose, e.g. Avicel PH101, Avicel PH102, Ceolus KG-802, Prosolv SMCC 50 or SMCC90 or other pharmaceutically acceptable grades of microcrystalline cellulose, as well as mixtures thereof.

The lamotrigine-containing particles (e.g., crystals, granules, or drug-layered beads) of the compositions of the present invention can also be coated with a taste-masking layer to improve the palatability of the composition. The lamotrigine-containing particles can be taste-masked by coating the lamotrigine-containing particles (e.g., crystals, granules, or drug-layered beads) with a water-insoluble polymer. Non-limiting examples of suitable water-insoluble polymers for the taste-masking layer include ethylcellulose, polyvinyl acetate (PVA), cellulose acetate (CA), cellulose acetate butyrate (CAB), methacrylate copolymers, such as those available under the tradename "EUDRAGIT" (e.g., type RL, RS, and NE30D), and combinations thereof.

In one embodiment, the water-insoluble polymer is ethylcellulose having a viscosity of about 90-110 cps when tested in an Ubbelohde viscometer as a 5 weight % 80:20 toluene/ethanol solution at 25° C.

In one embodiment, the ODT compositions of the present invention comprise about 25-35% of lamotrigine crystals, microencapsulated with a taste-masking layer comprising a water-insoluble polymer (e.g., ethylcellulose); about 60-70% of rapidly-dispersing granules (e.g., comprising crospovidone and mannitol); about 5% of additional disintegrant (e.g., crospovidone); about 1% of one or more flavors, and about 0.5%-1% of a sweetener (e.g., sucralose).

Because coating the lamotrigine-containing particles (e.g., crystals, granules, or drug-layered beads) with a water-insoluble polymer will reduce the release-rate of the lamotrigine, the taste-masking coating can also include a water-soluble or gastrosoluble pore-former. Gastrosoluble pore-formers are insoluble in water and saliva, but are readily soluble under acidic conditions, such as those found in the stomach. Non-limiting examples of water-soluble pore-formers include, e.g. sodium chloride, sucrose, povidone, and mixtures thereof. Non-limiting examples of gastrosoluble pore-formers include, e.g. calcium carbonate, magnesium citrate, magnesium hydroxide, and mixtures thereof. The ratio of water-insoluble polymer to water-soluble or gastrosoluble pore-former for producing taste-masked lamotrigine-containing granules may typically vary from about 95/5 to about 50/50. The amount of the taste-masking coating ranges from about 5% to about 30%, by weight of the taste-masked lamotrigine-containing granule, or about 5%-25%, about 5%-20%, about 5%-15%, about 5%-10%, about 10%-30%, about 10%-25%, about 10%-20%, about 10%-15%, about 15%-30%, about 50%-25%, about 15%-20%, about 20%-30%, about 20%-25%, or about 25%-30%.

One embodiment of a method for producing pleasant tasting lamotrigine ODT formulations of the present invention, comprising lamotrigine microparticles with a mean particle size of about 100-400 μm, comprises (i) preparing drug-containing cores having lamotrigine crystals with a desired mean particle size, e.g., as microgranules, lamotrigine particles (e.g., crystals), or as drug-layered beads, (ii) preparing granules comprising a disintegrant, a sugar alcohol and/or a saccharide, and (iii) compressing a blend comprising the lamotrigine microparticles and the disintegrant granules, optionally with pharmaceutically acceptable flavorant(s), sweetener(s), other disintegrant(s), colorant(s) and/or compression aides such as microcrystalline cellulose in sufficient quantities into the ODT form using a tablet press, such as a rotary tablet press equipped with an external lubrication system to lubricate the punches and dies prior to compression. These ODT tablets rapidly disintegrate upon exposure to the saliva in the mouth into a smooth, easy-to-swallow suspension with no gritty aftertaste.

In another embodiment, the method for preparing ODT formulations of the present invention comprising lamotrigine microparticles with a mean particle size of about 100-400 μm can also include a unit process for taste-masking the lamotrigine-containing particles (e.g., lamotrigine crystals, lamotrigine-containing granules or drug-layered beads) by coacervation or fluid bed coating prior to blending and compression into ODT tablets. For example, lamotrigine crystalline material with an average particle size range of about 1-200 μm, more particularly about 50-150 μm can be coated with a taste-masking layer by either fluid-bed coating or solvent coacervation in accordance with other aspects of the invention. Lamotrigine crystalline material with a mean particle size of about 5-50 μm can also be taste-masked by solvent coacervation as described herein.

The method of producing drug-layered beads in one embodiment of the invention comprises dissolving or suspending lamotrigine in a polymeric binder solution and layering onto inert particles (50-100 mesh or 150-300 μm in diameter) such as sugar spheres or cellulose spheres (e.g., Celphere® CP-203) using a fluid-bed coater equipped with a bottom-spray Wurster insert. These lamotrigine-coated beads can then be taste-masked by fluid-bed coating or by solvent coacervation as described herein.

In another embodiment, the method of preparing the compositions of the present invention includes a taste-masking step. The taste-masked lamotrigine-containing particles of the compositions of the present invention (e.g., lamotrigine crystals, lamotrigine-containing microgranules or drug-layered beads) of the present invention can be prepared by various methods, including solvent coacervation with a water-insoluble polymer such as ethylcellulose. The water-insoluble polymer (e.g., ethylcellulose), a phase-inducer (e.g., polyethylene), and lamotrigine are loaded into a coacervation tank containing cyclohexane. The mixture in the tank is heated to about 80° C. to dissolve the ethylcellulose, and then slowly cooled under controlled conditions thereby causing phase-induced microencapsulation of lamotrigine particles by the ethylcellulose. Microencapsulation or coacervation refers to the process of applying a membrane by phase separation for imparting taste-masking (or sustained release) properties. Upon reaching ambient temperature, the suspension of microencapsulated lamotrigine particles are filtered, washed with fresh cyclohexane and dried to reduce residual solvent levels within acceptable limits (e.g., <4,000 ppm), in one embodiment less than 1,000 ppm. The coating weight of the microencapsulated lamotrigine particles can range from about 5% to about 30% including about 10%, 15%, 20%, and 25%, inclusive of all ranges and subranges therebetween. Examples of such a coacervation process are disclosed in U.S. Pat. Nos. 5,252,337, 5,639,475, 6,139,865 and 6,495,160, each of which are herein incorporated by reference in their entirety for all purposes.

Alternatively, the coacervation solution can comprise a mixture of the water-insoluble polymer (e.g., ethylcellulose) and a water-insoluble or gastrosoluble pore-former (e.g., calcium carbonate). The ratio of water-insoluble polymer to pore-former can range from about 50/50 to 95/05, including about 55/45, about 60/40, about 65/35, about 70/30, about 75/25, about 80/20, about 85/15, and about 90/10, including all ranges and subranges therebetween. The coating weight of the microencapsulated lamotrigine particles can range from about 5% to about 30% including about 10%, 15%, 20%, and 25%, inclusive of all ranges and subranges therebetween. In one embodiment, the coacervation step comprises suspending the drug-containing particles in a solution of water-insoluble ethylcellulose at 80° C. in the coacervation tank. During the cooling cycle, the micronized pore-former is introduced into the tank at a temperature of about 58° C., while constantly stirring the suspension to uniformly distribute the pore-former in the microcapsule-membrane, at the farming/hardening phase. Examples of such a coacervation process are disclosed in U.S. patent application Ser. No. 11/213,266, which is herein incorporated in its entirety by reference for all purposes.

In another embodiment, the compositions of the present invention can be orally disintegrating tablets prepared by mixing lamotrigine microgranules or taste-masked lamotrigine microparticles, one or more flavoring agents, a sweetener, rapidly-dispersing microgranules, microcrystalline cellulose, and an additional disintegrant, and compressing this mixture into orally disintegrating tablets. The orally disintegrating tablets formed thereby rapidly disintegrate on contact with saliva in the buccal cavity, and have a pleasant taste (good creamy mouth feel) and provide rapid, substantially-complete release of the dose in the stomach.

In yet another embodiment, the composition of the present invention is an orally disintegrating tablet formed by compressing a composition comprising lamotrigine-containing particles, rapidly-dispersing granules, and optionally flavoring agents, sweeteners, and other pharmaceutically acceptable excipients in a tablet press equipped with an externally lubricating system to pre-lubricate dies and punches, thereby providing a tablet formulation otherwise free of lubricant. The orally disintegrating tablets thus produced typically exhibit sufficient hardness and sufficiently low friability to be suitable for packaging in HDPE bottles and push-through film backed or peel-off paper backed blister packs using conventional equipment for storage, transportation and commercial distribution.

The pharmaceutical composition of the present invention (e.g., ODT compositions comprising lamotrigine microgranules or taste-masked microparticles as described herein) will provide acceptable taste-masking when placed in the mouth until swallowed (e.g., not more than about 10% of the lamotrigine dose released in about 3 minutes when tested for dissolution in simulated saliva fluid at pH of about 7.0). The ODT will disintegrate in about 30 seconds when evaluated using the USP <701> Disintegration Test. The ODT will typically disintegrate on contact with saliva in the buccal cavity in about 60 seconds, forming a smooth, easy-to swallow suspension of taste-masked microparticles with an acceptable aftertaste. These taste-masked microparticles will typically provide substantially complete release of the lamotrigine dose upon entering the stomach (e.g., not less than about 60%, more particularly not less than 70% of the dose released in about 30 minutes when tested for dissolution in simulated gastric fluid or 0.01N HCl).

In another embodiment, a method of manufacturing orally disintegrating tablets of the present invention comprises the following steps:
(a) preparing lamotrigine-containing microgranules by granulating crystalline lamotrigine material having an average particle size of about 5-50 μm and one or more diluents/fillers such as lactose, mannitol, microcrystalline cellulose and mixtures thereof, with a polymeric binder in a high-shear granulator or a fluid-bed coater;
(b) granulating one or more sugar alcohols and/or saccharides, each having an average particle diameter of not more than about 30 μm, with a disintegrant such as crospovidone, using water or an alcohol-water mixture in a conventional granulator, and drying the granulate in fluid-bed equipment or a conventional oven to produce rapidly-dispersing microgranules with an average particle size of not more than about 400 μm, as described in U.S. patent application Ser. No. 10/827,106, filed Apr. 19, 2004;
(c) blending the lamotrigine microgranules of step (a) with one or more flavoring agents, a sweetener, microcrystalline cellulose, additional disintegrant, and the rapidly-dispersing microgranules of step (b); and
(d) compressing the blend of step (c) into tablets using e.g. a conventional rotary tablet press equipped with an external lubrication system to pre-lubricate the dies and punches.

In another embodiment, a method of manufacturing orally disintegrating tablets of the present invention comprises the following steps:
a) preparing a drug-containing core particle (e.g., lamotrigine crystals, drug-layered beads, or lamotrigine-containing microgranules) by granulating the drug and optionally one or more diluents/fillers such as lactose, mannitol, microcrystalline cellulose and mixtures thereof with a polymeric binder in a high-shear granulator or a fluid-bed coater, or drug-layering on an inert particle (60-100 mesh sugar sphere or cellulose sphere, e.g., Celphere® CP-203) from a solution/suspension comprising a polymeric binder and the drug in a fluid-bed coater and optionally applying a seal-coat (e.g., Opadry® Clear);
b) taste-masking core particles by microencapsulation, e.g. by solvent coacervation or fluid-bed coating with a water-insoluble polymer such as ethylcellulose, or with a mixture of a water-insoluble functional polymer and a water-soluble/gastrosoluble pore-former (e.g., ethylcellulose and sodium chloride or calcium carbonate at a ratio ranging from about 50/50 to 95/5) to produce pleasant-tasting microparticles with a desired particle size distribution (e.g., an average particle size of not more than about 400 μm, or an average particle size of not more than about 300 μm);
c) granulating one or more sugar alcohols and/or saccharides, each of which has an average particle diameter of not more than about 30 μm, with a disintegrant such as crospovidone, as disclosed herein;
d) blending the taste-masked microparticles of step (b) with one or more flavoring agents, a sweetener, microcrystalline cellulose, additional disintegrant, and rapidly-dispersing microgranules of step (c); and
e) compressing the blend of step (d) into tablets using e.g. a conventional rotary tablet press equipped with an external lubrication system to pre-lubricate the dies and punches.

In Vitro Disintegration Time/Dissolution Testing

Disintegration times were measured using the USP <701> Disintegration Test procedures. The taste-masking property of the taste-masked microparticles and the orally disintegrating tablets may be evaluated in the mouth by determining the percentage of drug-release when tested for dissolution using USP Apparatus 2 (paddles @ 75 rpm) in 900 mL of salivasimulating fluid at a pH of about 6.8-7.0 (a release of not more than about 10% of the dose in about 3 minutes is considered acceptable). In addition, the rapid-release property in the stomach of the taste-masked microparticles and the orally disintegrating tablets may be evaluated by determining the percentage of drug-release when tested for dissolution using USP Apparatus 2 (paddles @ 75 rpm) in 900 mL of 0.01N HCl at 37.0±0.5° C. (a release of not less than about 70% of the dose in about 30 minutes is considered acceptable). The potency of the tablets and the percentage of drug dissolved at different time points are determined using a validated HPLC methodology using a 150×4.6 mm stainless steel column packed with 3 μm Phenomenex Luna C18 or an alternative suitably validated methodology.

Compositions of the present invention (e.g. ODT compositions) comprising lamotrigine microgranules in accordance with one embodiment exhibit the following properties:

(1) acceptable hardness and friability suitable for packaging in bottles and blister packaging, storage, transportation and commercial distribution;
(2) disintegration on contact with saliva in the oral cavity in about 60 seconds forming a smooth, easy-to-swallow suspension with a pleasant taste (no grittiness or aftertaste), meeting the specification of not more than 30 seconds in the <USP 701> Disintegration Test; and
(3) lamotrigine microgranules provide rapid, substantially-complete release of the dose upon entry into the stomach, as evident by meeting the dissolution specifications of more than about 10% of the dose in about 3 minutes in a simulated saliva buffer at pH 6.8 and not less than about 75% of the dose in about 30 minutes in 900 mL of 0.01N HCl buffer when tested for dissolution using USP Apparatus 2 (paddles @ 75 rpm).

In another embodiment, the pharmaceutical ODT composition of the present invention comprises lamotrigine crystalline material taste-masked by solvent coacervation with ethylcellulose, and exhibits the following properties:

1) exhibits acceptable hardness and friability in order to be suitable for packaging in bottles and blisters for storage, transportation and commercial distribution;
2) disintegrates on contact with saliva in the oral cavity in about 60 seconds forming a smooth, easy-to-swallow suspension with a pleasant taste (no grittiness or aftertaste), meeting the specification of not more than 30 seconds in the USP <701> Disintegration Test; and
3) rapid, substantially-complete release of the close upon entry into the stomach, meeting the dissolution specifications of more than about 10% of the dose in about 3 minutes in a simulated saliva buffer at pH 6.8 and not less than about 75% of the dose in about 30 minutes in 0.01N HCl buffer when tested for dissolution using USP Apparatus 2 (paddles @ 75 rpm in 900 mL buffer).

The compositions of the present invention are useful in treating epilepsy and/or bipolar disorder, and contain a therapeutically effective amount of lamotrigine. The compositions of the present invention can comprise about 1-250 mg of lamotrigine, including 2 mg, 5 mg, 25 mg, 50 mg, 100 mg, 150 mg, and 200 mg of lamotrigine. The compositions of the present invention can be administered according to any suitable dosage schedule as can be readily determined by a physician. For example, the compositions of the present invention can be administered in a single daily dose, or multiple daily doses, depending upon the severity of the condition, and physical condition of the patient.

The following non-limiting examples illustrate the compositions of the present invention, comprising microgranules, taste-masked microparticles or the orally disintegrating tablet dosage form, wherein the composition comprising lamotrigine, taste-masked or otherwise. The compositions of the present invention are prepared as described herein, and exhibit acceptable organoleptic properties when placed in the mouth and substantially complete, rapid-release of the close on entry into the stomach.

EXAMPLE 1

Lamotrigine Microgranules A: Mannitol 25 (69.4% w/w) and Crospovidone XL-10 (3.7% w/w) at a ratio of 95/5 were co-milled individually by passing the mixture through a Comil® milling apparatus, equipped with 0.225" spacers, at a speed of about 1400-1500 rpm. The mannitol, crospovidone, and lamotrigine crystalline material from Teva (26.9% w/w) were blended for about 3-5 minutes to mix the ingredients. A Glatt GPCG-3 fluid-bed apparatus equipped with a top spray granulation chamber and a granulation bowl was charged with the pre-blend of mannitol, crospovidone, and lamotrigine (batch size: 1500 g) and granulated by spraying purified water (nozzle: 1.2 mm tip) at an atomization pressure of about 1.25 bar and at a spray rate of 30-50 mL/min and an outlet temperature of >70° C. and at a product temperature of >33° C. The wet mass was dried until the moisture level (the percent loss on drying) was less than about 1%.

Lamotrigine Microgranules B: Mannitol 25 (59.8% w/w) and Crospovidone XL-10 (3.1% w/w) at a ratio of 95/5 were co-milled individually by passing the mixture through a Comil® milling apparatus, equipped with 0.225" spacers, at a speed of about 1400-1500 rpm. The mannitol, erospovidone, as well as pre-staged calcium carbonate (10% w/w), and lamotrigine crystalline material from Glaxo SmithKline (26.9% w/w) were blended for about 3-5 minutes to mix the ingredients and granulated by spraying an aqueous solution of hydroxypropylcellulose (Klucel LF; 0.2% w/w) in the same Glatt as described above.

Lamotrigine Microgranules C: Lactose monohydrate (35.0% w/w) and lamotrigine crystalline material from Glaxo SmithKline (26.9% w/w) were blended for about 3-5 minutes to mix the ingredients. Hydroxypropylcellulose (Klucel LF; 5.0% w/w) was slowly added to water in a stainless steel container and dissolved, and agitated to achieve an appreciable vortex. The lactose-lamotrigine blend was granulated in the Glatt 3 by spraying the aqueous binder solution at a spray rate of 25-50 mL/min as described above.

Lamotrigine Microgranules D: Mannitol 25 (58.5% w/w) and Crospovidone XL-10 (3.1% w/w) at a ratio of 95/5 were co-milled individually by passing the mixture through a Comil® mill. The mannitol, crospovidone, as well as pre-staged microcrystalline cellulose (Avicel PH 101 at 10.0% w/w) and lamotrigine crystalline material from Glaxo Smith-Kline (26.9% w/w) were blended for about 3-5 minutes to mix the ingredients. Hydroxypropylcellulose (Klucel LF; 1.5% w/w) was slowly added to water in a stainless steel container and dissolved, and agitated to achieve an appreciable vortex. The above blend was granulated in the Glatt 3 by spraying the aqueous binder solution at a spray rate of 25-50 mL/min as described above. Granulations were also prepared by reducing the binder content to 0.2% w/w.

Lamotrigine ODT, 200 mg: Sucralose, cherry or peppermint flavor, Crospovidone XL-10 and microcrystalline cellulose were pre-blended and blended with lamotrigine microgranules A, B, C, or D and compressed at different compression forces into 200 mg orally disintegrating tablets (ODTs) 14 or 15 mm in diameter and weighing 800-1,000 mg to optimize tabletting parameters—weight (target: 800 mg), hardness, friability (target: <0.6%), disintegration time (target: <30 seconds), dissolution, taste, mouthfeel, aftertaste (grittiness), flavor or sweetener content. Compositions and/or compression conditions were varied to evaluate the robustness of the formulations. Lamotrigine ODT tablets, 25-mg, 50-mg, and 100-mg, whenever compressed, were compressed using the same compression blends and were dose proportional to the 200-mg ODT tablets.

Tabletting: A Hata production tablet press equipped with a vacuum transfer system, tablet de-duster, a metal detector, and a Matsui Ex-lube system were set up according to standard operating procedures. Magnesium stearate was used as a processing aid, i.e., to externally lubricate the punch and die surfaces and was therefore present in only trace amounts on the tablets. The weight range for the tablets was typically ±5% of the target tablet weight. The Ex-lube system was started to ensure that the lubricant was spraying properly when the tablet press was running. The tabletting parameters, such as fill depth (mm), pre-compression position (mm or kN) and main compression position (mm or kN) were adjusted on the press in order to produce 25 mg tablets that meet the exemplary specifications listed below:

| Tablet Parameters | Target | Range |
|---|---|---|
| Weight per tablet (mg) | 100 | 95-105 (±5%) |
| Thickness (mm) | 2.40 | 2.00-2.80 |
| Hardness (N) | 28 | 8-48 |
| Friability (%) | NMT 0.6 | NMT 1.0 |
| Weight/10 tablets (g) | 1.00 | 0.96-1.04 (±4%) |

Following the successful set-up, the press was run in 'Automatic Mode' until completion. During the run, tablets were sampled periodically to ensure that the tablets produced would meet the specifications listed above.

EXAMPLE 2

Lamotrigine Microcaps at 10% Coating: A 5-gallon coacervation tank equipped with an agitator blade 6"+4" high shear, 3-blade insert, was charged with 10 kg of cyclohexane, and 1350 g lamotrigine crystalline material, 150 g ethylcellulose (Ethocel Standard 100 Premium), 100 g polyethylene (Epoline C-10) were charged into the tank. The tank was heated to approximately 80° C. while stirring at about 200 rpm to dissolve the ethylcellulose. Thereafter, the tank was subjected to controlled-cooling to induce phase separation. Upon cooling to ambient temperature, the microcapsules were filtered, rinsed with fresh cyclohexane, and filtered material was transferred to a fume hood to allow residual cyclohexane to evaporate, thereby providing lamotrigine Microcaps with a taste-masked coating of 10% by weight.

Lamotrigine Microcaps at 15 or 20% Coating: Lamotrigine Microcaps coated with ethylcellulose at 15% or 20% by weight were prepared using a method similar to that described above.

Lamotrigine Microcaps at 10% (Ethylcellulose+Pore-Former) Coating: Microcapsules were also prepared by charging the 5-gallon tank with 1080 g lamotrigine, 270 g micronized calcium carbonate (gastrosoluble pore-former), 150 g ethylcellulose, and 100 g Epoline, C-10, using a method similar to that described above.

Rapidly Dispersing Microgranules: Rapidly dispersing microgranules may comprise a sugar alcohol such as mannitol and/or a saccharide such as lactose and a super disintegrant such as Crospovidone XL-10. The sugar alcohol and/or saccharide and disintegrant will typically be present in the rapidly dispersing microgranules at a ratio of from about 99:1 to about 90:10 (sugar alcohol and/or saccharide:disintegrant). For example, D-mannitol, a sugar alcohol with an average particle size of about 15 μm and Crospovidone XL 10, a super disintegrant, may be used at a ratio of about 95/5 in a high shear granulator using purified water as the granulating fluid and dried by spreading the granulated mixture on trays in a heated convection oven.

Lamotrigine ODT 25 and 200 mg: Sucralose, Cherry or Peppermint flavor, Crospovidone XL-10, and microcrystalline cellulose were pre-blended and blended with Rapidly Dispersing Microgranules and Lamotrigine Microcaps at 10%, 15%, 20% or 10% (ethylcellulose+pore-former) coating by weight, and compressed at different compression forces into 200 mg orally disintegrating tablets (ODTs) 14 or 15 mm in diameter and weighing 800-1,000 mg to optimize tabletting parameters: weight (target: 800 mg), hardness, friability (target: <0.6%), disintegration time (target: <30 seconds), dissolution, taste, mouthfeel, aftertaste (grittiness), flavor or sweetener content. Compositions and/or compression conditions were varied to evaluate the robustness of the formulations.

EXAMPLE 3

Lamotrigine Microgranules: Mannitol 25 (58.75% w/w) and Crospovidone XI, 10 (3.10% w/w) at a ratio of 95/5 were co-milled individually by passing the mixture through a Comil® mill. The mannitol, crospovidone, as well as pre-staged microcrystalline cellulose (Avicel PH 101 at 10.00% w/w) and lamotrigine crystalline material from Glaxo Smith-Kline (26.90% w/w) were blended for about 3-5 minutes to mix the ingredients. Hydroxypropylcellulose (Klucel LF; 1.25% w/w) was slowly added to water in a stainless steel container and dissolved, and agitated to achieve an appreciable vortex. The above blend was granulated in the Glatt 3 by spraying the aqueous binder solution at a spray rate of 50 mL/min as described above. Two additional batches of granules were also prepared as described above.

Prototypes 1-3 for Sensory Testing: Refer to Table 1 below for details of the compositions of Prototypes 1 to 3. A pre-blend consisting of sucralose, Cherry or Spearmint flavor and Crospovidone XL-10 was first prepared by blending these ingredients in a 0.25 cu-ft V-blender. Lamotrigine microgranules from above were then blended into the mixture. The resulting composition was then compressed into 100 mg orally disintegrating tablets 11 mm in diameter and weighing 400 mg (Prototype 1; 1220-NHV-056) or into 200 mg orally disintegrating tablets 14 mm in diameter and weighing 800 mg (Prototype 2; 1220-NHV-088 and Prototype 3 (1220-NHV-072).

TABLE 1

Compositions of Lamotrigine Prototypes

| Ingredients (%) | Prototype 1 (100 mg Cherry) | Prototype 2 (200 mg Spearmint) | Prototype 3 (200 mg Cherry) |
|---|---|---|---|
| Lamotrigine Granules | 90.91 | 92.94 | 93.61 |
| Crospovidone XL-10 | 7.09 | 5.16 | 4.39 |
| Sucralose | 0.50 | 0.4 | 0.50 |
| Cherry 376120 | 1.50 | — | 1.50 |
| Spearmint 376120 | — | 1.50 | — |
| Total | 100.0 | 100.0 | 100.0 |

Lamotrigine Microcaps® at 15% Coating: A 5-gallon coacervation tank equipped with an agitator blade 6"+4" high shear, 3-blade insert, was charged with 10 kg of cyclohexane, and 850 g lamotrigine crystalline material, 150 g ethylcellulose (Ethocel Standard 100 Premium), 100 g polyethylene (Epoline C-10) were charged into the tank. The tank was heated to approximately 80° C. while stirring at about 200 rpm to dissolve the ethylcellulose. Thereafter, the tank was subjected to controlled-cooling to induce phase separation. Upon cooling to ambient temperature, the microcapsules were filtered, rinsed with fresh cyclohexane, and filtered material was transferred to a fume hood to allow residual cyclohexane to evaporate to provide lamotrigine Microcaps® with a taste-masked coating of 15% by weight. An additional batch of Microcaps® was prepared using the same procedure.

Prototypes 4 & 5 for Sensory Testing: A pre-blend consisting of 0.4% sucralose, 1.0% cherry (364450) flavor and 5% Crospovidone XL-10 was first prepared by blending these ingredients in a 0.25 cu-ft V-blender. Rapidly Dispersing Microgranules (64.19% w/w) and Lamotrigine Microcapules (29.41% w/w) from Ex. 2 were then blended into the mixture. The resulting composition was then compressed into 100 mg orally disintegrating tablets 11 mm in diameter and weighing 400 mg (prototype 4; 1220-NHV-104) or into 200 mg orally disintegrating tablets 14 mm in diameter and weighing 800 mg (prototype 5; 1220-NHV-120).

Figure 3:
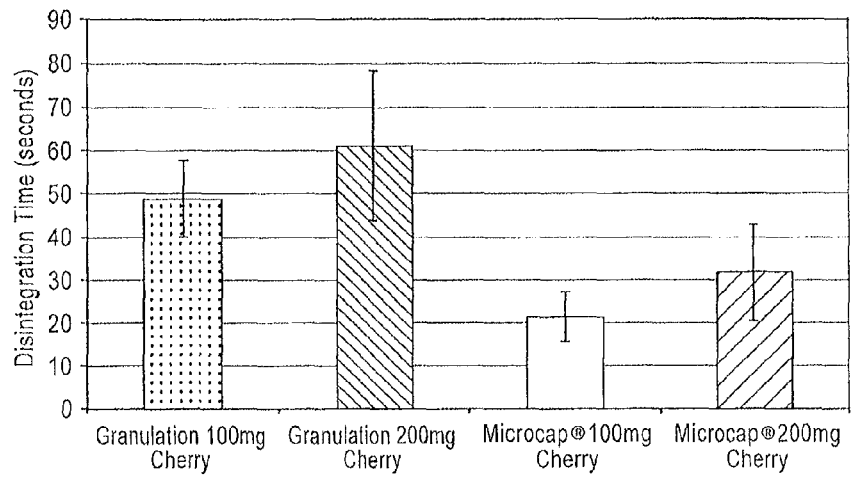
FIG. 3 compares the oral (in vivo) disintegration times of ODT formulations comprising lamotrigine microgranules vs. microcapsules of Example 3.
Figure 4:
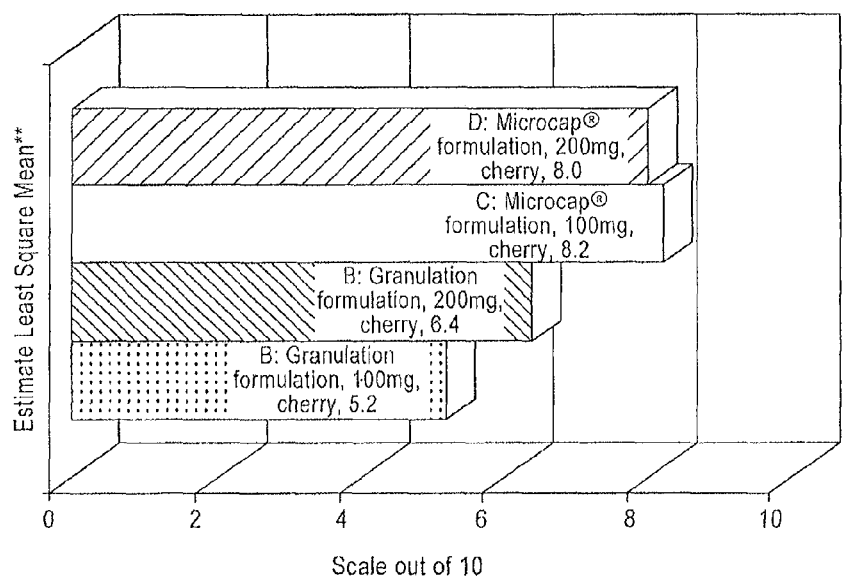
FIG. 4 compares the taste/flavor ranking results for ODT formulations comprising lamotrigine microgranules vs. microcapsules of Example 3.
Figure 5:
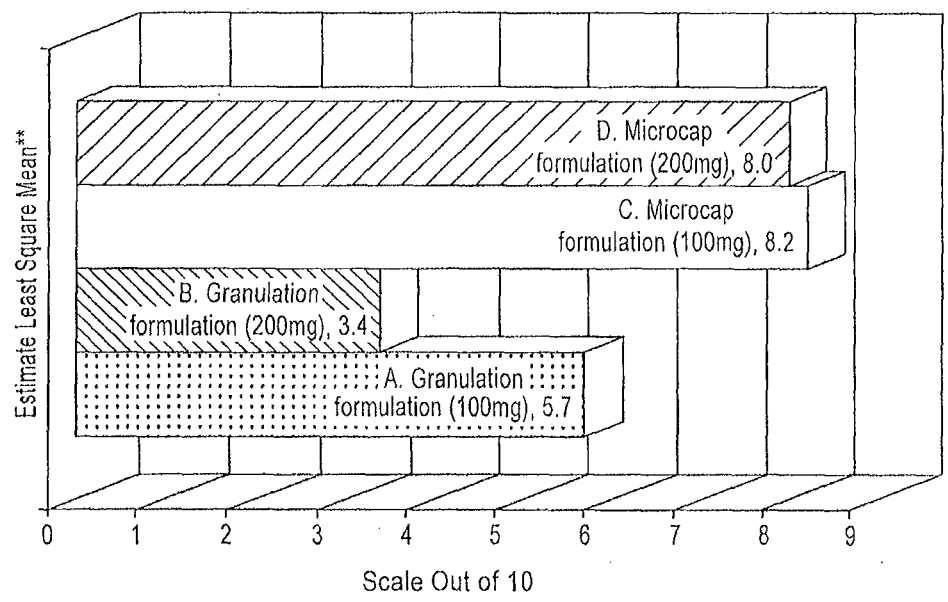
FIG. 5 compares the aftertaste ranking results for ODT formulations comprising lamotrigine microgranules vs. microcapsules of Example 3.

The dissolution profile for Prototypes 1-3 and 4-5 are respectively shown in FIG. 1 and FIG. 2. An organoleptic evaluation of ODT Prototypes (1 and 3 based on granulation approach and 4-5 based on Microcap® approach) using a randomized, blinded, cross-over design in 9 healthy male volunteers 18-55 years of age, was used to evaluate taste, in vivo disintegration time (the actual time in seconds for the tablet to disintegrate in the mouth), mouthfeel and aftertaste [Bitterness scale: 1 (very bitter)-5 (further taste-masking needed)-10 (pleasant taste)] and flavor/sweetener [balance scale: 1 (low, need to increase)-8 (optimum)-10 (over-powering, need to reduce)]. The results of DT, taste/flavor, and aftertaste are presented in FIGS. 3 to 5, and also summarized below.

Results from Sensory Testing:
Statistical analysis proved differences between the Microcap® formulations and the Granulation formulations were statistically significant, and that Microcap® formulations had superior dissolution time, taste/flavor, and aftertaste properties compared to the granulation formulations.
Microcaps® formulations exhibited considerably improved disintegration time compared to granulation formulations.
Microcaps® formulations exhibited significantly higher scores on both taste and aftertaste compared to granulation formulations.
There were no significant differences in mouthfeel between the Microcaps® and granulation formulations—both were acceptable.
There were no significant differences between Microcaps® formulations at the two different strengths—both were acceptable.

EXAMPLE 4

Lamotrigine Microgranules: A Glatt GPCG 120 was charged with 48.8 kg of lamotrigine, 103.7 kg of mannitol USP (Mannitol 25 Co-milled), and 5.5 kg of crospovidone, NF XL-10 (Co-milled). The powder blend was granulated by spraying it with an aqueous solution of hydroxypropylcellulose (KIucel LF; 1.25% w/w) at 4.0 bar and at a spray rate of 900-1200 g/min and dried for an LOD of <1.0%.

Lamotrigine Microcaps®: The lamotrigine microgranules prepared as described above (78.3 kg), Ethocel 100 cps (13.8 kg) and Epolene (9.2 kg) were transported onto the hopper of a 500-gallon coacervation tank containing 312.5 gallons cyclohexane. The agitator was set to approximately 40 rpm, and the above materials were charged into the coacervation tank under inert nitrogen atmosphere. The encapsulation process was carried out in 'Automatic Mode'. At steady state, the agitator speed was approximately 68 (66-70) rpm, the tank temperature was approximately 81° C. (78-85° C.). Upon reaching ambient temperature following controlled cooling, the composition was vacuum filtered/rinsed with fresh cyclohexane, and the resulting microencapsulated material was dried in the fluid-bed dryer per the drying subroutine on the dryer (i.e., an inlet temperature of 25° C. to 99° C., inlet airflow of 2500 cu-ft per minute, and drying time of 3-5 hours). The dried Microcaps® were sieved through a Kason siever into a clean, 30-gallon fiber drum lined with two, 4 mil polyethylene bags. A similar procedure was used in the 200-gallon coacervation tank/fluid-bed dryer system.

Lamotrigine ODT, 25 and 200 mg: Sucralose (0.40% w/w) and crospovidone (5.0% w/w) were pre-blended by passing the mixture through a Comil® to achieve homogeneity. Similarly, cherry flavor (1.0% w/w) was pre-blended with a small amount of the rapidly-dispersing microgranules (64.19% w/w), and the two pre-blended mixtures were blended until homogeneous. Taste-masked microparticles were prepared as described above (29.41% w/w) and the remaining rapidly-dispersing microgranules were blended together and further blended with the above blend containing the erospovidone, the flavor, and the sweetener and the blends with a batch size of 75.0 Kg to 501-626 kg were manufactured.

EXAMPLE 5

Pilot PK Study in Humans: A 4-arm, randomized pilot PK (pharmacokinetics) study was conducted in 16 healthy adult subjects, to compare lamotrigine formulations according to the present invention with conventional lamotrigine immediate release (IR) formulations, e.g., Lamictal®. Lamictal®, an immediate release (IR) formulation, is rapidly and almost completely absorbed after oral administration of the dosage forms (98% absolute bioavailability), generating peak serum concentrations of 1.3 to 4.7 hours. The elimination half life after a single dose is about 33 hours. Oral clearance is approximately doubled and $t_{1/2}$ is reduced to approximately 15 hrs in the presence of enzyme-inducing anti-epileptic drugs like carbamazepine.

Four dosage forms were compared: A: 25 mg lamotrigine immediate release (IR), B: 25 mg lamotrigine ODT, C: 200 mg lamotrigine IR, and 200 mg lamotrigine ODT. The ODT dosage forms were prepared in accordance with the methods of the present invention (e.g., Example 4 using lamotrigine Microcaps® produced in the 200-gallon system). Blood samples were withdrawn from the subjects at 0, 0.25, 0.5, 0.75, 1, 1.25, 1.5, 1.75, 2, 2.5, 3, 4, 5, 6, 8, 10, 12, 16, and 24 hour time points, and plasma concentrations were determined bioanalytically. The plasma concentration profiles are presented in FIGS. 6 to 8 and the PK parameters are presented in Tables 2 and 3, below. The ODT formulations administered were judged to be bioequivalent to the respective lamotrigine (Lamictal®) IR tablets.

TABLE 2

PK Parameters for Lamotrigine ODT vs Ref

| PK Parameter | $T_{lag}$ (hrs) | | $T_{max}$ (hrs) | | $C_{max}$ (ng/mL) | | AUC (ng · hr/mL) | |
|---|---|---|---|---|---|---|---|---|
| | 25 mg ODT | 25 mg IR | 25 mg ODT | 25 mg IR | 25 mg ODT | 25 mg IR | 25 mg ODT | 25 mg IR |
| Arithmetic Mean | — | — | — | — | 0.368 | 0.382 | 5.98 | 5.89 |
| Median | 0.00 | 000 | 2.00 | 1.60 | 0.383 | 0.365 | 6.07 | 5.77 |
| Geometric Mean | — | — | — | — | 0.364 | 0.368 | 5.92 | 5.76 |
| Minimum | 0.00 | 0.00 | 0.50 | 0.25 | 0.276 | 0.228 | 4.87 | 3.89 |
| Maximum | 0.50 | 0.00 | 4.00 | 3.00 | 0.482 | 0.689 | 8.17 | 8.08 |
| CV % | — | — | — | — | 16.1 | 30.1 | 14.6 | 21.6 |
| | 200 mg ODT | 200 mg IR | 200 mg ODT | 200 mg IR | 200 mg ODT | 200 mg IR | 200 mg ODT | 200 mg IR |
| Arithmetic Mean | — | — | — | — | 2.89 | 3.25 | 49.0 | 51.8 |
| Median | 0.00 | 0.00 | 2.25 | 1.00 | 2.75 | 3.03 | 47.5 | 49.6 |
| Geometric Mean | — | — | — | — | 2.85 | 3.18 | 48.4 | 50.8 |
| Minimum | 0.00 | 0.00 | 0.75 | 0.5 | 2.21 | 2.35 | 36.0 | 40.4 |
| Maximum | 0.25 | 0.00 | 8.00 | 4.0 | 3.95 | 5.08 | 63.6 | 81.2 |
| CV % | — | — | — | — | 17.9 | 22.3 | 16.1 | 23.1 |

TABLE 3

Pilot PK Data for Lamotrigine ODT vs IR

| PK Parameter | Comparison | Geometric $LS_{mean}$ for Test | Geometric $LS_{mean}$ for Ref. | Ratio of Test/Ref (90% CI) |
|---|---|---|---|---|
| $AUC_{0-24\ hr}$ (ng * hr/mL) | 25-mg ODT vs 25-mg IR | 5.922 | 5.760 | 1.028 (0.934-1.131) |
| | 200-mg ODT vs 200-mg IR | 48.409 | 47.522 | 1.019 (0.922-1.125) |
| $C_{max}$ (ng/mL) | 25-mg ODT vs 25-mg IR | 0.364 | 0.368 | 0.988 (0.880-1.110) |
| | 200-mg ODT vs 200-mg IR | 2.850 | 2.994 | 0.952 (0.844-1.073) |

EXAMPLE 6

Lamotrigine IR Beads: Hydroxypropylcellulose (Klucel LF; 20 g) is slowly added to a 95/5 acetone/water mixture to dissolve while constant stirring. Lamotrigine (180 g) is slowly added to the binder solution until dissolved. A Glatt GPCG equipped with a bottom spray Wurster insert is charged with 900 g of 60-80 mesh sugar spheres. The drug layering solution is sprayed at an atomization pressure of 1.5 bar and at a spray rate of 10-30 mg/min while maintaining the product temperature at approximately 30-33° C. These drug-layered heads are provided with a 2% seal-coat of Opadry® Clear to produce IR beads with a drug loading of about 20% by weight.

Lamotrigine Taste-Masked Beads: IR beads are membrane coated by spraying-coating a solution of ethylcellulose and gastrosoluble micronized calcium carbonate at a ratio of 70/30 for a weight gain of approximately 10% based on the total weight of the coated bead.

Lamotrigine ODT, 25 mg, 50 mg: sucralose (0.5%), cherry flavor 1.0%) and FD&C Blue No. 2 (0.2%), and crospovidone (5%) are pre-blended in a 0.25 cu-ft V-blender and further blended with the lamotrigine taste-masked heads prepared above (43%), and rapidly-dispersing microgranules (50.3%) prepared as described herein (see Example 2), and compressed into 25-mg and 50-mg ODT tablets weighing approximately 400 and 800 mg respectively, using methods as described herein.

It is to be understood that while the invention has been described in conjunction with specific embodiments thereof, that the description above as well as the examples that follow are intended to illustrate and not limit the scope of the invention. Any modification within the scope of the invention will be apparent to those skilled in the art to which the invention pertains.

All documents cited herein are incorporated by reference in their entirety for all purposes. The citation of any document is not to be construed as an admission that it is prior art with respect to the present invention.

What is claimed is:

1. An ODT composition consisting essentially of:
   a therapeutically effective amount of lamotrigine microcapsules comprising 25 or 200 mg of lamotrigine crystals having an average particle size of about 1-50 μm, coated with a taste-masking layer comprising a pharmaceutically acceptable water-insoluble polymer;
   a disintegrant; and
   a sugar alcohol, a saccharide, or both a sugar alcohol and a saccharide;
   wherein after a single oral administration said ODT composition provides:
   a $C_{max}$ in the range of 0.276 to 0.482 ng/mL of lamotrigine,
   an $AUC_{0-24}$ in the range of 4.87 to 8.17 ng·hr/mL of lamotrigine, or
   both a $C_{max}$ in the range of 0.276 to 0.482 ng/mL of lamotrigine and an $AUC_{0-24}$ in the range of 4.87 to 8.17 ng·hr/mL of lamotrigine,
   if the total amount of lamotrigine in the ODT is 25 mg, or
   a $C_{max}$ in the range of 2.21 to 3.95 ng/mL of lamotrigine, an $AUC_{0-24}$ in the range of 36.0 to 63.6 ng·hr/mL of lamotrigine, or
   both a $C_{max}$ in the range of 2.21 to 3.95 ng/mL of lamotrigine and an $AUC_{0-24}$ in the range of 36.0 to 63.6 ng·hr/mL of lamotrigine, if the total amount of lamotrigine in the ODT is 200 mg.

2. The ODT composition of claim 1, wherein the disintegrant is selected from the group consisting of crospovidone, sodium starch glycolate, crosslinked sodium carboxymethyl cellulose, low substituted hydroxypropyl cellulose, and mixtures thereof.

3. The ODT composition of claim 1, wherein the sugar alcohol is selected from the group consisting of arabitol, isomalt, erythritol, glycerol, lactitol, mannitol, sorbitol, xylitol, maltitol, and mixtures thereof.

4. The ODT composition of claim 1, wherein the saccharide is selected from the group consisting of glucose, fructose, lactose, ribose, sucrose, maltose, trehalose, cellobiose, and mixtures thereof.

5. The ODT composition of claim 1, wherein the water-insoluble polymer is selected from the group consisting of ethylcellulose, polyvinyl acetate, cellulose acetate, cellulose acetate butyrate, and water-insoluble methacrylate copolymers.

6. The ODT composition of claim 1, wherein the ODT composition consists essentially of the lamotrigine microcapsules, the disintegrant, and a sugar alcohol, wherein the sugar alcohol is selected from the group consisting of arabitol, isomalt, erythritol, glycerol, lactitol, mannitol, sorbitol, xylitol, maltitol, and mixtures thereof.

7. The ODT composition of claim 2, wherein the ODT composition consists essentially of the lamotrigine microcapsules, the disintegrant, and a sugar alcohol, wherein the sugar alcohol is selected from the group consisting of arabitol, isomalt, erythritol, glycerol, lactitol, mannitol, sorbitol, xylitol, maltitol, and mixtures thereof.

8. The ODT composition of claim 1, wherein the ODT composition consists essentially of the lamotrigine microcapsules, the disintegrant, and a saccharide, wherein the saccharide is selected from the group consisting of glucose, fructose, lactose, ribose, sucrose, maltose, trehalose, cellobiose, and mixtures thereof.

9. The ODT composition of claim 2, wherein the ODT composition consists essentially of the lamotrigine microcapsules, the disintegrant, and a saccharide, wherein the saccharide is selected from the group consisting of glucose, fructose, lactose, ribose, sucrose, maltose, trehalose, cellobiose, and mixtures thereof.

10. The ODT composition of claim 1, wherein the ODT composition substantially disintegrates within about 60 seconds after administration in the oral cavity of the patient.

11. The ODT composition of claim 10, wherein the ODT composition substantially disintegrates within about 30 seconds after administration in the oral cavity of the patient.

12. The ODT composition of claim 1, wherein the ODT composition disintegrates within about 30 seconds when tested by the <USP 701> Disintegration Test.

13. The ODT composition of claim 1, wherein the ODT composition releases about 70% or more of the total dose of lamotrigine upon entering the stomach of a patient.

14. The ODT composition of claim 1, wherein the ODT composition releases about 70% or more of the total amount of lamotrigine in 30 min when tested for dissolution using United States Pharmacopoeia Apparatus 2 (paddles @75 rpm in 900 mL of 0.01 N HCl buffer).

15. The ODT composition of claim 1, further comprising additional pharmaceutically acceptable ingredients selected from the group consisting of a filler, a flavor, a sweetener, a colorant, and combinations thereof.

16. The ODT composition of claim 1, wherein the ODT composition provides a $C_{max}$ in the range of 0.276 to 0.482 ng/mL of lamotrigine, if the total amount of lamotrigine in the ODT is 25 mg.

17. The ODT composition of claim 1, wherein the ODT composition provides an $AUC_{0-24}$ in the range of 4.87 to 8.17 ng·hr/mL of lamotrigine, if the total amount of lamotrigine in the ODT is 25 mg.

18. The ODT composition of claim 1, wherein the ODT composition provides a $C_{max}$ in the range of 0.276 to 0.482 ng/mL of lamotrigine and an $AUC_{0-24}$ in the range of 4.87 to 8.17 ng·hr/mL of lamotrigine, if the total amount of lamotrigine in the ODT is 25 mg.

19. The ODT composition of claim 1, wherein the ODT composition provides a $C_{max}$ in the range of 2.21 to 3.95 ng/mL of lamotrigine, if the total amount of lamotrigine in the ODT is 200 mg.

20. The ODT composition of claim 1, wherein the ODT composition provides an $AUC_{0-24}$ in the range of 36.0 to 63.6 ng·hr/mL of lamotrigine, if the total amount of lamotrigine in the ODT is 200 mg.

21. The ODT composition of claim 1, wherein the ODT composition provides a $C_{max}$ in the range of 2.21 to 3.95 ng/mL of lamotrigine and an $AUC_{0-24}$ in the range of 36.0 to 63.6 ng·hr/mL of lamotrigine, if the total amount of lamotrigine in the ODT is 200 mg.

22. A method of treating a mood disorder, or treating seizures comprising administering to a patient in need thereof a therapeutically effective amount of the ODT of claim 1.

* * * * *